United States Patent

Ouchi

[11] Patent Number: 6,152,922
[45] Date of Patent: Nov. 28, 2000

[54] HIGH-FREQUENCY SNARE FOR ENDOSCOPE

[75] Inventor: Teruo Ouchi, Saitama, Japan

[73] Assignee: Asahi Kogaku Kogyo Kabushiki Kaisha, Tokyo, Japan

[21] Appl. No.: 09/339,197

[22] Filed: Jun. 24, 1999

[30] Foreign Application Priority Data

Jul. 27, 1998 [JP] Japan ................................ 10-210493

[51] Int. Cl.⁷ .................................................. A61B 18/18
[52] U.S. Cl. ............................................................ 606/47
[58] Field of Search ............................. 606/41–49, 106, 606/110, 113; 607/96, 98, 99, 113, 116

[56] References Cited

U.S. PATENT DOCUMENTS

| | | | |
|---|---|---|---|
| 4,493,320 | 1/1985 | Treat | 606/47 |
| 4,503,855 | 3/1985 | Maslanka | 606/47 |
| 5,885,278 | 3/1999 | Fleischman | 606/41 |
| 5,911,739 | 6/1999 | Kordis et al. | 607/122 |

FOREIGN PATENT DOCUMENTS

| | | |
|---|---|---|
| 61-7695 | 3/1986 | Japan . |
| 61-44502 | 10/1986 | Japan . |

*Primary Examiner*—Linda C. M. Dvorak
*Assistant Examiner*—R. Kearney
*Attorney, Agent, or Firm*—Greenblum & Bernstein, P.L.C.

[57] ABSTRACT

A high-frequency snare for an endoscope has an electrically conductive control wire axially movably inserted in an electrically insulating sheath. A wire loop formed from an electrically conductive elastic wire is connected at the rear end thereof to the control wire. A distal end tip is attached to a bent portion at the distal end of the wire loop. The distal end tip has a pair of parallel through-holes. Two approximately parallel portions of the elastic wire bent in a U-shape at the bent portion of the wire loop are loosely passed through the through-holes, respectively, without being secured to the distal end tip.

9 Claims, 7 Drawing Sheets

HIGH-FREQUENCY SNARE FOR ENDOSCOPE

BACKGROUND OF THE INVENTION

The present disclosure relates to subject matter contained in Japanese Patent Application No. 10-210493 (filed on Jul. 27, 1998), which is expressly incorporated herein by reference in its entirety.

1. Field of the Invention

The present invention relates to a high-frequency snare that is removably inserted into an instrument-inserting channel of an endoscope to carry out excision of a polyp or the like in a body cavity.

2. Description of the Prior Art

Figure 9:
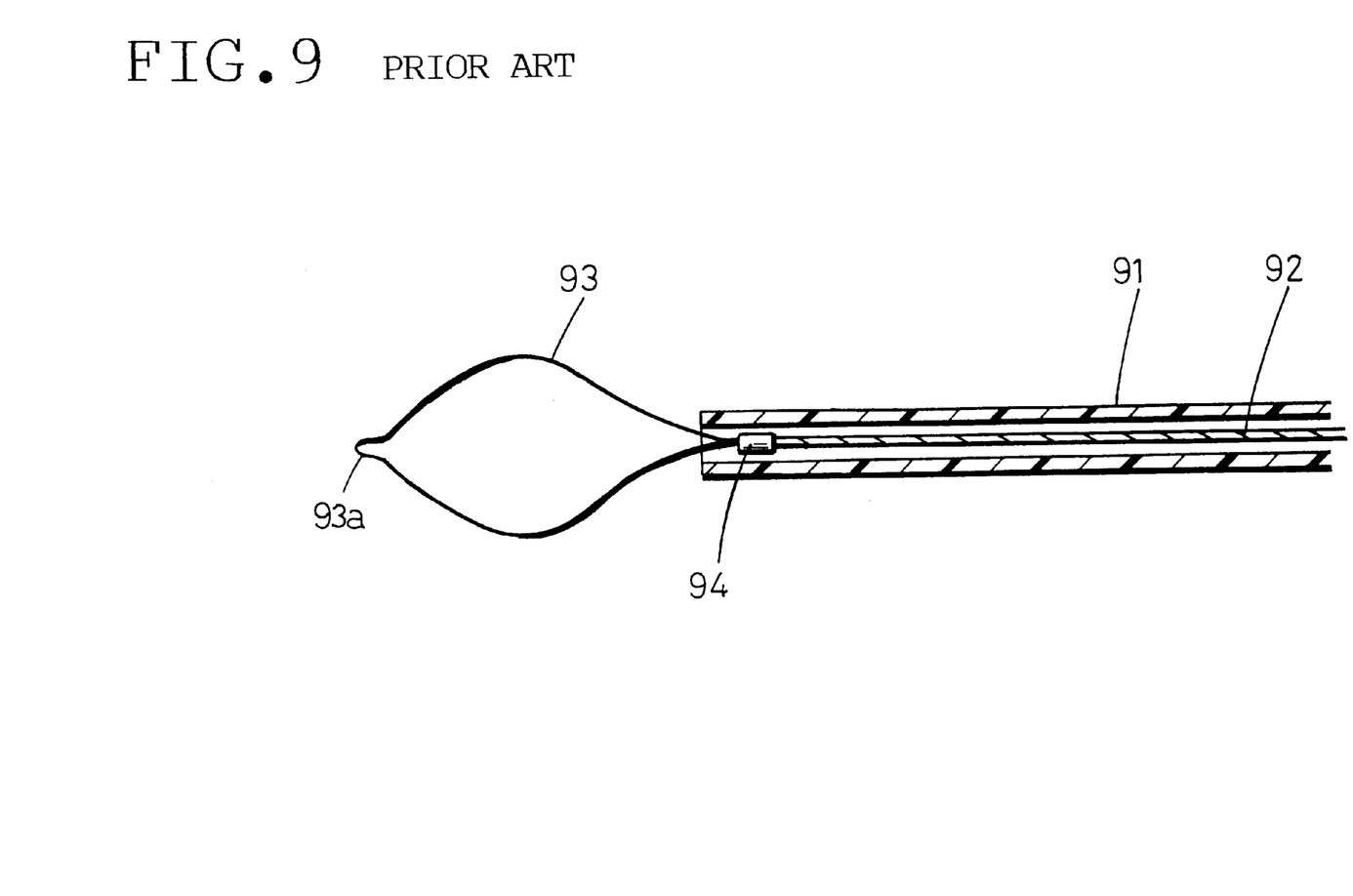
FIG. 9 is a sectional plan view of a distal end portion of a conventional high-frequency snare for an endoscope.

In general, a high-frequency snare for an endoscope is arranged as illustrated in FIG. 9. A single electrically conductive elastic wire is bent into a U-shape at the distal end thereof and looped at the rear of the U-shaped bent portion to form a wire loop 93. The rear end of the wire loop 93 is connected to an electrically conductive control wire 92 axially movably inserted in an electrically insulating sheath 91. When the control wire 92 is pushed from the proximal end of the sheath 91, the wire loop 93 projects from the distal end of the sheath 91 to expand in a loop shape. When the control wire 92 is pulled, the wire loop 93 withdraws into the distal end of the sheath 91 to contract.

Figure 10:
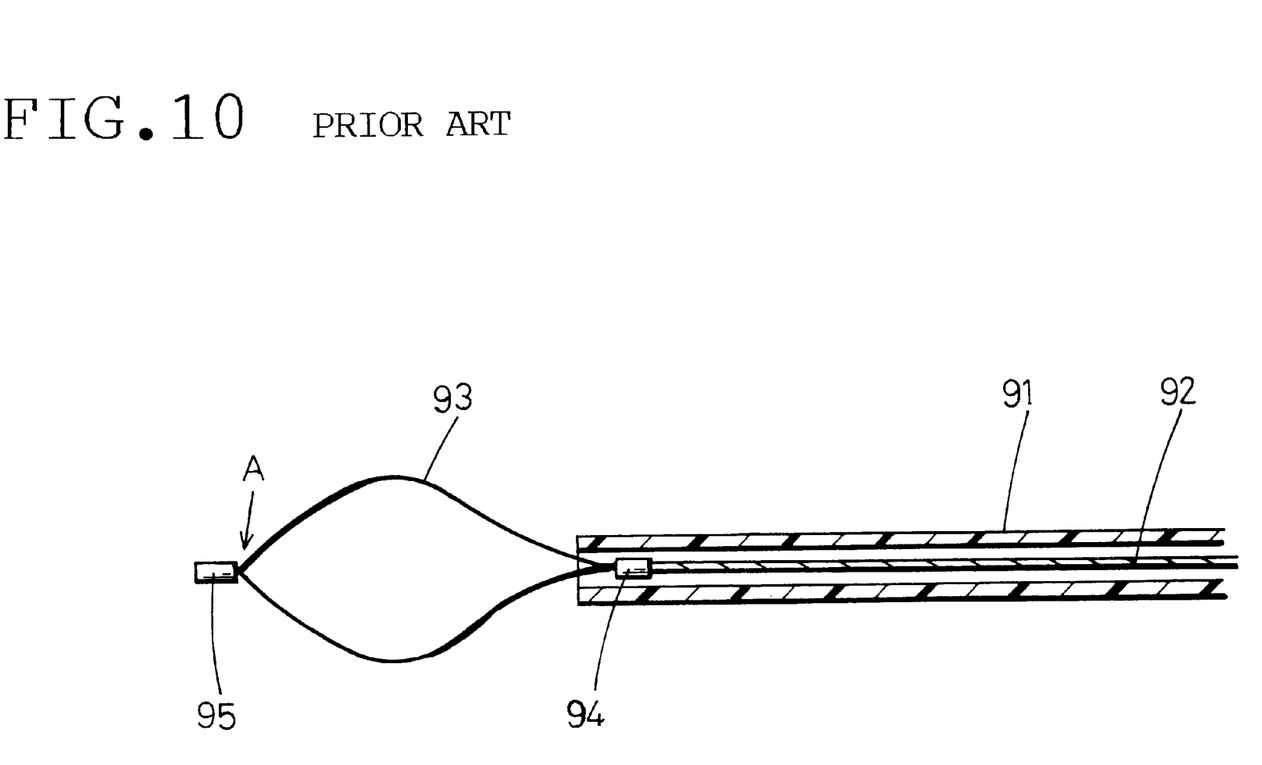
FIG. 10 is a sectional plan view of a distal end portion of another conventional high-frequency snare for an endoscope.

As illustrated in FIG. 10, there is another conventional high-frequency snare for an endoscope in which a distal end tip 95 is secured to the bent end portion of the wire loop 93.

However, in the high-frequency snare for an endoscope in which a loop is formed simply by bending an elastic wire as shown in FIG. 9, when a polyp is caught in the wire loop 93 and pinched tight therewith, large stress concentration occurs at the bent end portion 93a in the expanding direction. Therefore, there are not a few cases where when the high-frequency snare is repeatedly used, the bent end portion 93a is deteriorated and broken.

In the high-frequency snare in which the distal end tip 95 is secured to the distal end of the wire loop 93 as shown in FIG. 10, when the wire loop 93 expands and contracts, stress concentration occurs at the boundary A between the loop portion of the wire loop 93 and the secured distal end portion thereof. Therefore, it is also likely that the portion A of the wire loop 93 will be deteriorated and broken when the high-frequency snare is repeatedly used.

SUMMARY OF THE INVENTION

An object of the present invention is to provide a high-frequency snare for an endoscope in which the elastic wire is not readily deteriorated even when the wire loop is repeatedly expanded and contracted, and which is therefore excellent in durability.

Other objects and advantages of the present invention will become apparent from the following detailed description of illustrated embodiments of the invention.

According to the present invention, there is provided a high-frequency snare for an endoscope that has an electrically conductive control wire axially movably inserted in an electrically insulating sheath. A wire loop is formed by bending an electrically conductive elastic wire in a U-shape. The wire loop is connected at the rear end thereof to the control wire. When the control wire is pushed from the proximal end of the sheath, the wire loop projects from the distal end of the sheath to expand in a loop shape. When the control wire is pulled, the wire loop withdraws into the distal end of the sheath to contract. The high-frequency snare includes a distal end tip attached to a bent portion at the distal end of the wire loop. The distal end tip has a pair of parallel through-holes. Two approximately parallel portions of the elastic wire bent in a U-shape at the bent portion of the wire loop are loosely passed through the through-holes, respectively, without being secured to the distal end tip.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Embodiments of the present invention will be described below with reference to the accompanying drawings.

Figure 1:
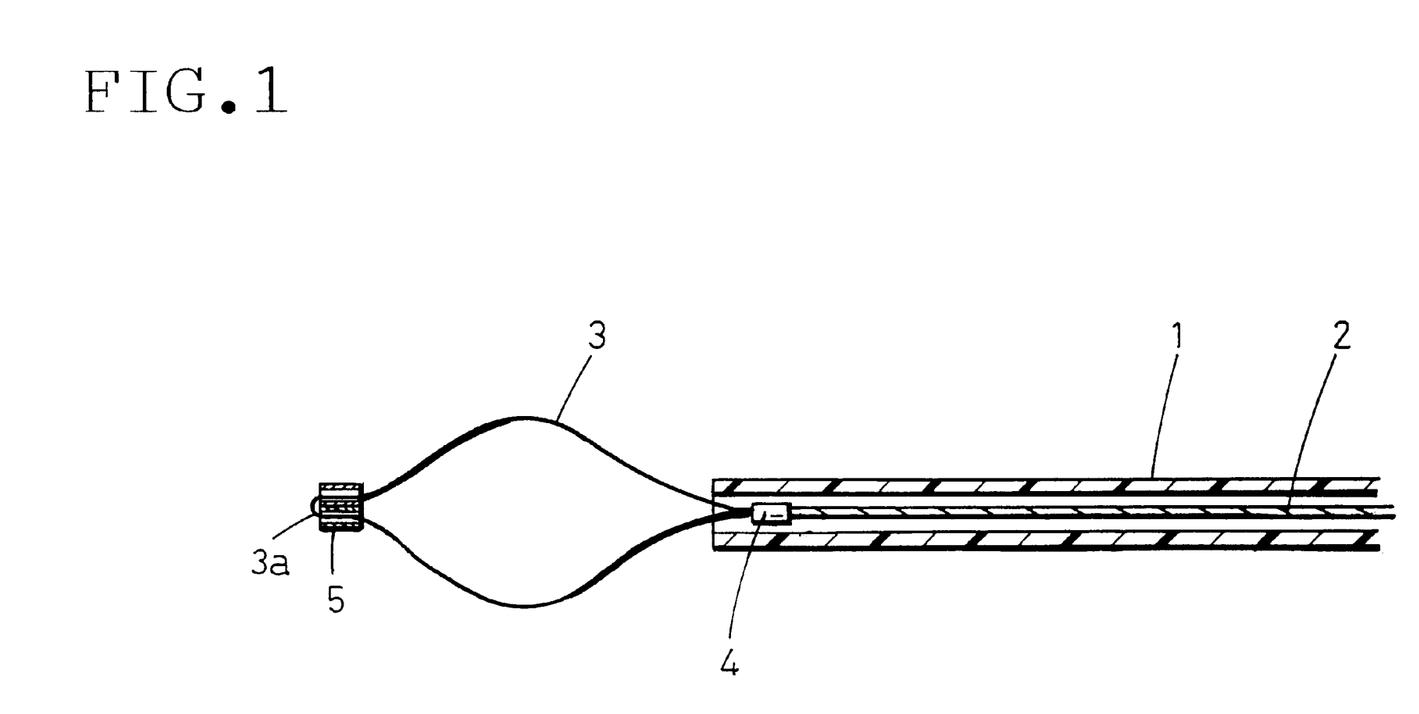
FIG. 1 is a sectional plan view of a distal end portion of a high-frequency snare for an endoscope according to a first embodiment of the present invention.

FIGS. 1 shows a high-frequency snare for an endoscope according to a first embodiment of the present invention. A flexible sheath 1 is removably inserted into an instrument-inserting channel of an endoscope (not shown). The sheath 1 is formed from an electrically insulating flexible tube, for example, a tetrafluoro-ethylene resin tube.

A control wire 2 made of an electrically conductive metal is axially movably inserted in the sheath 1 over the entire length thereof. The movement of the control wire 2 is controlled at a control part (not shown) that is connected to the proximal end of the sheath 1.

A wire loop 3 is connected through a connecting pipe 4 to the distal end of the control wire 2 by soldering or the like. The wire loop 3 is formed from an elastic wire made of an electrically conductive metal and adapted to expand in a loop shape by its own elasticity. The wire loop 3 can be supplied with a high-frequency electric current from the proximal end of the sheath 1 through the control wire 2.

The wire loop 3 is formed from a single electrically conductive elastic wire. The wire loop 3 is bent into a U-shape at the distal end thereof to form a U-shaped bent end portion 3a. Under free conditions, the wire loop 3 expands in a smoothly curved shape (e.g. an oval shape). When pulled with the control wire 2, the wire loop 3 is withdrawn into the distal end portion of the sheath 1 and thus folded. When pushed out of the sheath 1, the wire loop 3 expands by its own elasticity.

A distal end tip 5 is attached to the bent end portion 3a of the wire loop 3. As shown in the enlarged view of FIG. 2, the distal end tip 5 is provided with a pair of parallel through-holes 5a. Two approximately parallel portions of the elastic wire bent in a U-shape at the bent end portion 3a are passed through the through-holes 5a, respectively.

Figure 2:
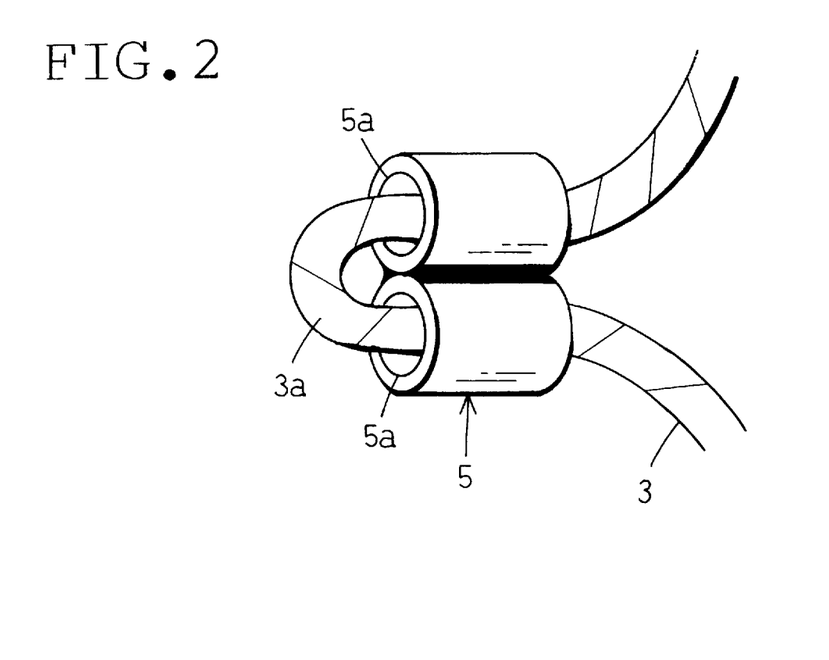
FIG. 2 is an enlarged perspective view of the distal end portion of the high-frequency snare according to the first embodiment of the present invention.

In this embodiment, the distal end tip 5 is formed by securing together two short electrically conductive metal cylinders in parallel by silver-alloy brazing, spot-welding or the like. However, the distal end tip 5 may also be formed from a drawn material having an 8-shaped cross-sectional configuration. It is also possible to form the distal end tip 5 from a plastic material by molding process.

The distal end tip 5 is not secured to the elastic wire, which forms the wire loop 3. The two portions of the elastic wire are loosely passed through the through-holes 5a of the distal end tip 5. However, the distal end tip 5 will not move from the distal end portion of the wire loop 3 because the elastic wire curves outward to a considerable extent near the rear end of the distal end tip 5 to form the wire loop 3.

Figure 3:
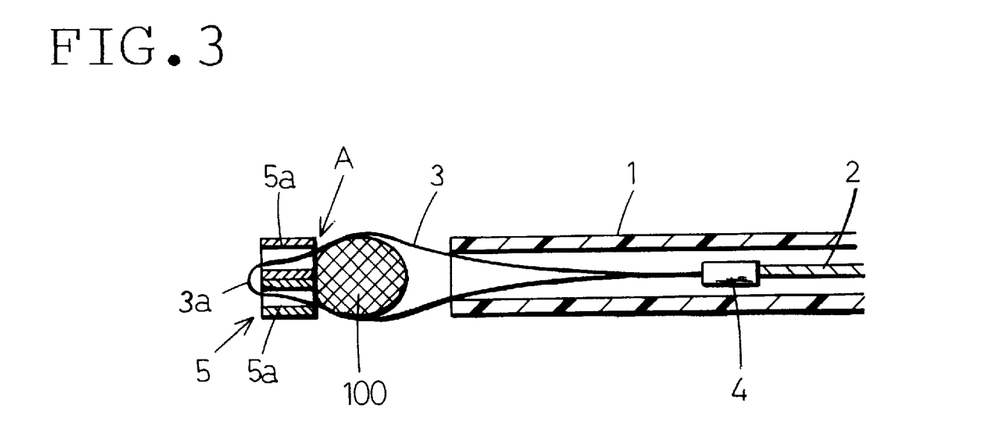
FIG. 3 is a sectional plan view of the distal end portion of the high-frequency snare according to the first embodiment of the present invention, showing a state where a polyp is pinched tight with the high-frequency snare.

FIG. 3 shows the high-frequency snare for an endoscope according to the embodiment arranged as stated above. In the figure, the high-frequency snare is inserted into an instrument-inserting channel of an endoscope (not shown), and a polyp 100 is pinched tight with the wire loop 3.

When the control wire 2 is pulled toward the proximal end of the sheath 1 to pinch the polyp 100 tight with the wire loop 3, strong force acts so as to expand the elastic wire at the bent end portion 3a. However, because the elastic wire extends through the respective through-holes 5a of the distal end tip 5, the angle of expansion is controlled. Consequently, excessive stress concentration will not occur on the elastic wire in the through-holes 5a. Accordingly, the rate of deterioration of the elastic wire is favorably low.

Furthermore, the elastic wire is not secured to the distal end tip 5 but loosely passed through the through-holes 5a. Therefore, at the boundary A between the distal end tip 5 and the wire loop 3, the elastic wire smoothly expands continuously from those portions thereof which lie in the through-holes 5a. Accordingly, at the boundary A also, excessive stress concentration will not occur on the elastic wire, and thus the rate of deterioration of the elastic wire is favorably low.

Accordingly, even if the high-frequency snare is repeatedly used for excision of a polyp or the like, the elastic wire, which forms the wire loop 3, deteriorates at a low rate. Therefore, the high-frequency snare can be used satisfactorily for a larger number of cases of disease than the conventional high-frequency snare.

Figure 4:
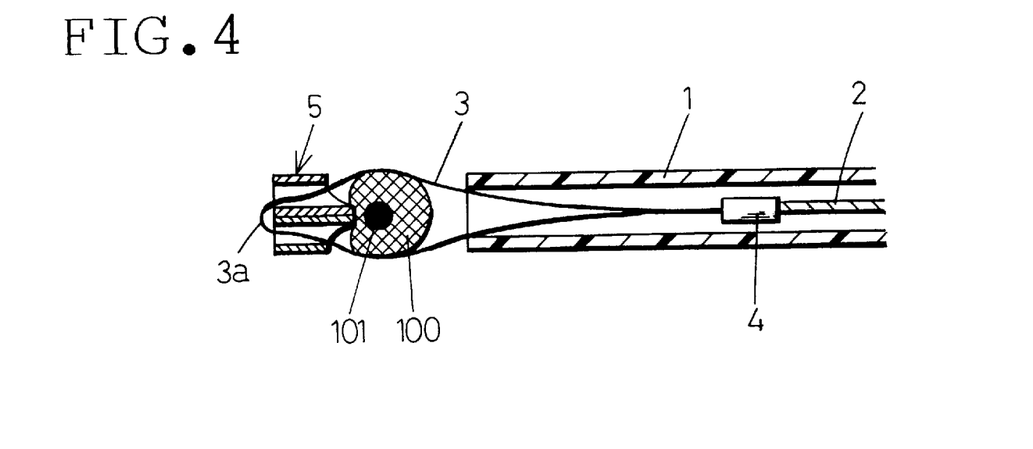
FIG. 4 is a sectional plan view of a distal end portion of a high-frequency snare for an endoscope according to a second embodiment of the present invention, showing a state where a polyp is pinched tight with the high-frequency snare.

FIG. 4 shows a high-frequency snare for an endoscope according to a second embodiment of the present invention. This embodiment differs from the first embodiment in the shape of the distal end tip 5, which is made of an electrically conductive metal.

Figure 5:
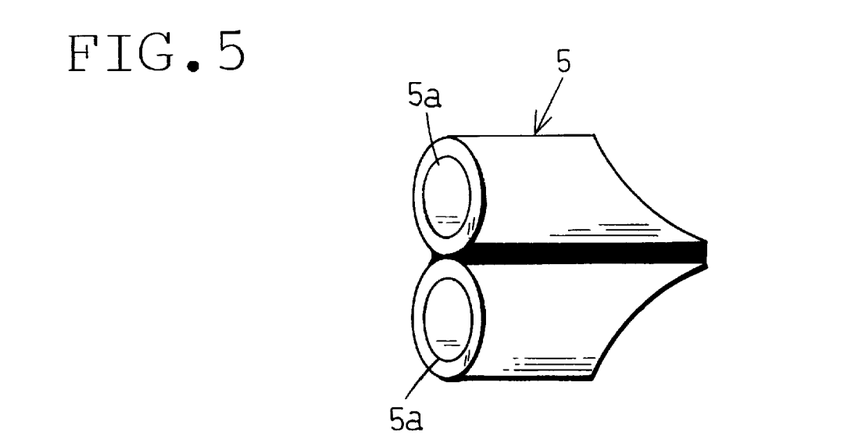
FIG. 5 is an enlarged perspective view of a distal end tip of the high-frequency snare according to the second embodiment of the present invention.

As shown in the enlarged view of FIG. 5, the distal end tip 5 is diagonally cut at the rear end thereof such that the central portion is longer than the peripheral portion. The rest of this embodiment is the same as in the first embodiment.

By virtue of the above-described arrangement, when a polyp 100 is pinched tight with the wire loop 3 as shown in FIG. 4, only the central portion at the rear end of the distal end tip 5 contacts the polyp 100. Therefore, cauterization is first effected toward a blood vessel 101 in the polyp 100. Consequently, it is possible to prevent bleeding when the blood vessel 101 is cut.

Figure 6:
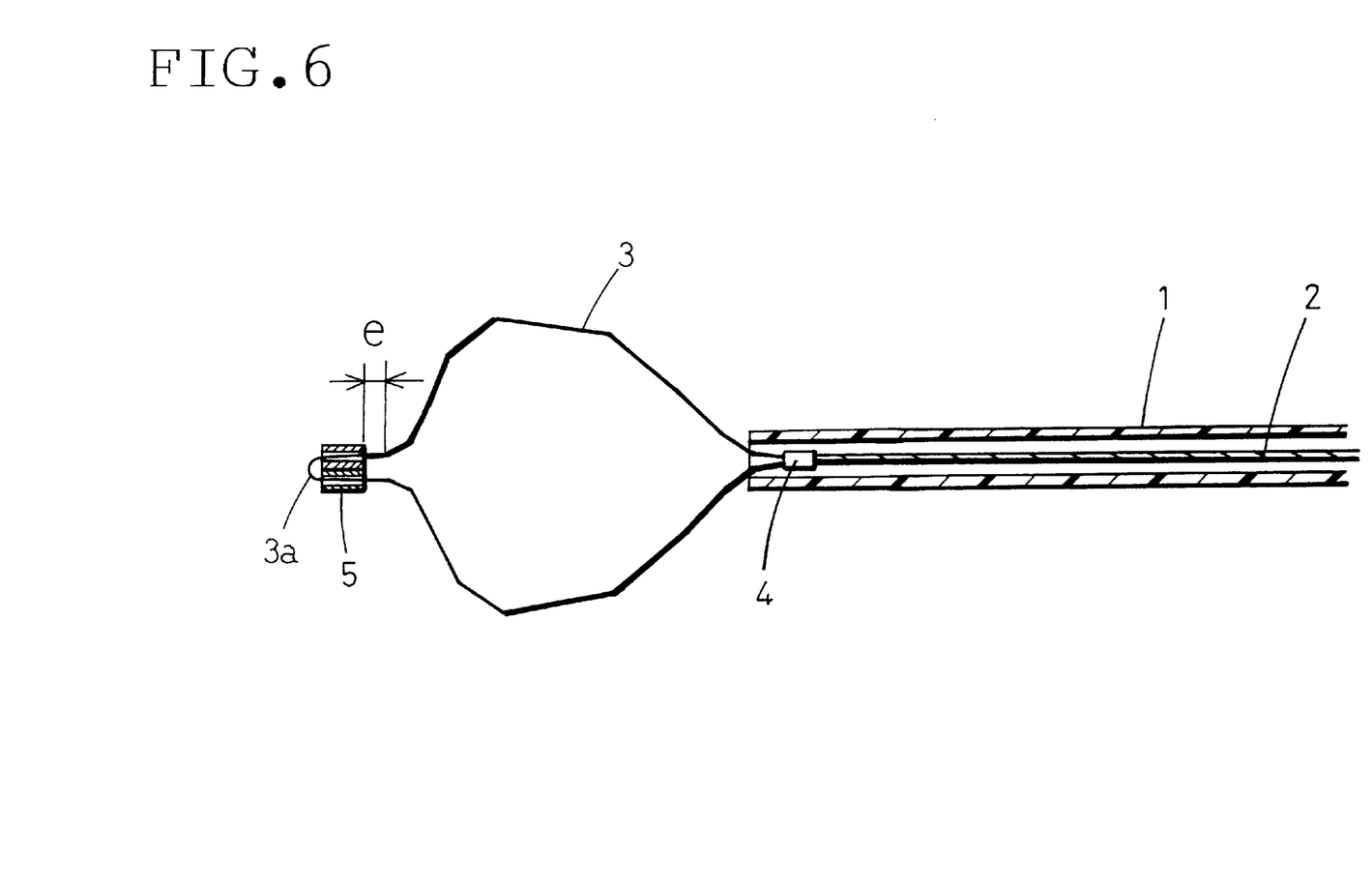
FIG. 6 is a sectional plan view of a distal end portion of a high-frequency snare for an endoscope according to a third embodiment of the present invention.

FIG. 6 shows a high-frequency snare for an endoscope according to a third embodiment of the present invention. In this embodiment, the wire loop 3 is formed in an expanded shape by bending an elastic wire at a plurality of points in an intermediate portion thereof. The arrangement of the rest of this embodiment is the same as in the first embodiment.

In a case where the wire loop 3 is formed by bending an elastic wire as in this embodiment, the distance e between the foremost bent portion and the distal end tip 5 should preferably be set approximately within the range of $0 \leq e \leq 3$ millimeters.

Figure 7:
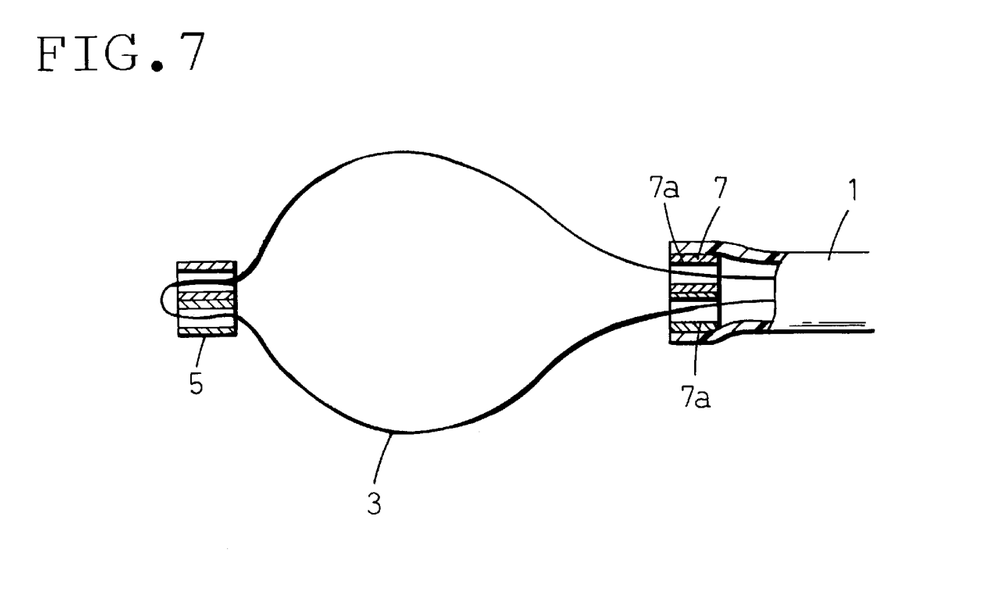
FIG. 7 is a sectional plan view of a distal end portion of a high-frequency snare for an endoscope according to a fourth embodiment of the present invention.

FIG. 7 shows a high-frequency snare for an endoscope according to a fourth embodiment of the present invention. In this embodiment, a wire-passing member 7 having the same shape as that of the distal end tip 5 is fitted to the distal end portion of the sheath 1, and the two end portions of the elastic wire are passed through a pair of through-holes 7a, respectively, of the wire-passing member 7.

Figure 8:
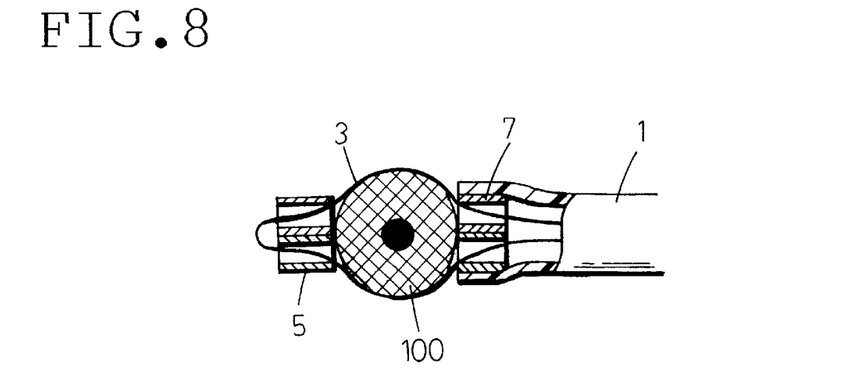
FIG. 8 is a sectional plan view of the distal end portion of the high-frequency snare according to the fourth embodiment of the present invention, showing a state where a polyp is pinched tight with the high-frequency snare.

With the above-described arrangement, when a polyp 100 is pinched tight with the wire loop 3 as shown in FIG. 8, the polyp 100 will not be drawn into the sheath 1. Therefore, the peripheral wall of the polyp 100 is surely cauterized, and the polyp 100 can be excised without bleeding.

If the wire-passing member 7 is formed of an electrically conductive metal, the polyp 100 is cauterized also at the area of contact with the wire-passing member 7 by a high-frequency electric current conducted from the wire loop 3 to the wire-passing member 7. Accordingly, the peripheral wall of the polyp 100 is cauterized even more surely, and the polyp 100 can be excised without bleeding even more effectively.

According to the present invention, a pair of parallel through-holes are formed in a distal end tip attached to a bent end portion that is formed at the distal end of a wire loop formed from an elastic wire, and two approximately parallel portions of the elastic wire bent in a U-shape at the bent end portion are loosely passed through the through-holes, respectively. Accordingly, when a polyp is pinched tight with the wire loop, the angle of expansion at the bent end portion of the elastic wire is controlled, and the elastic wire smoothly expands at the boundary between the distal end tip and the wire loop. Therefore, excessive stress concentration will not occur on the elastic wire. Even when the wire loop is repeatedly expanded and contracted, the elastic wire will not deteriorate. Thus, excellent durability is obtained.

While the invention has been described by reference to specific embodiments chosen for purposes of illustration, it should be apparent that numerous modifications could be made thereto by those skilled in the art without departing from the basic concept and scope of the invention.

What is claimed is:

1. A high-frequency snare for an endoscope, said high-frequency snare having an electrically conductive control wire axially movably inserted in an electrically insulating sheath, and a wire loop formed by bending an electrically conductive elastic wire in a U-shape, said wire loop being connected at a rear end thereof to said control wire, wherein when said control wire is pushed from a proximal end of said sheath, said wire loop projects from a distal end of said sheath to expand in a loop shape, whereas when said control wire is pulled, said wire loop withdraws into the distal end of said sheath to contract, said high-frequency snare comprising:

a distal end tip attached to a bent portion at a distal end of said wire loop, said distal end tip having a pair of parallel through-holes, wherein two approximately parallel portions of said elastic wire bent in a U-shape at said bent portion of said wire loop are loosely passed through said through-holes, respectively, without being secured to said distal end tip.

2. A high-frequency snare for an endoscope according to claim 1, wherein said distal end tip comprises two cylindrical members secured together in parallel.

3. A high-frequency snare for an endoscope according to claim 1, wherein said distal end tip is electrically conductive.

4. A high-frequency snare for an endoscope according to claim 3, wherein said distal end tip is diagonally cut at a rear end thereof such that a central portion is longer than a peripheral portion.

5. A high-frequency snare for an endoscope according to claim 1, wherein said wire loop is formed in a smoothly curved shape.

6. A high-frequency snare for an endoscope according to claim 1, wherein said wire loop is formed by bending said elastic wire at a plurality of points in an intermediate portion thereof.

7. A high-frequency snare for an endoscope according to claim 6, wherein a distance between a foremost bent portion of said elastic wire and a rear end of said distal end tip is not more than 3 millimeters.

8. A high-frequency snare for an endoscope according to claim 1, wherein a wire-passing member having a pair of parallel through-holes is fitted to a distal end portion of said sheath, and said two portions of said elastic wire are passed through said through-holes, respectively.

9. A high-frequency snare for an endoscope according to claim 8, wherein said wire-passing member is electrically conductive.

\* \* \* \* \*